United States Patent
Saur et al.

(10) Patent No.: US 12,357,398 B2
(45) Date of Patent: *Jul. 15, 2025

(54) MICROSCOPY SYSTEM AND METHOD FOR OPERATING THE MICROSCOPY SYSTEM

(71) Applicant: Carl Zeiss Meditec AG, Jena (DE)

(72) Inventors: Stefan Saur, Aalen (DE); Christian Voigt, Abtsgmuend (DE); Marco Wilzbach, Stuttgart (DE); Christoph Hauger, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/492,776

(22) Filed: Oct. 23, 2023

(65) Prior Publication Data

US 2024/0058075 A1 Feb. 22, 2024

Related U.S. Application Data

(63) Continuation of application No. 17/856,977, filed on Jul. 2, 2022, now Pat. No. 11,806,092, which is a
(Continued)

(30) Foreign Application Priority Data

Apr. 25, 2018 (DE) ...................... 10 2018 206 406.7

(51) Int. Cl.
*A61B 8/14* (2006.01)
*A61B 34/20* (2016.01)
(Continued)

(52) U.S. Cl.
CPC .............. *A61B 34/20* (2016.02); *A61B 90/39* (2016.02); *G02B 21/0012* (2013.01); *G06T 7/13* (2017.01);
(Continued)

(58) Field of Classification Search
CPC . A61B 34/20; A61B 90/39; A61B 2034/2055; A61B 2090/3937; G06T 2207/30204
See application file for complete search history.

(56) References Cited

U.S. PATENT DOCUMENTS

| | | | |
|---|---|---|---|
| 5,098,426 A | 3/1992 | Sklar et al. |
| 5,820,545 A | 10/1998 | Arbter et al. |

(Continued)

FOREIGN PATENT DOCUMENTS

| | | | |
|---|---|---|---|
| CA | 2948719 A1 | 9/2014 |
| CN | 1045028 A | 9/1990 |

(Continued)

OTHER PUBLICATIONS

Nicola Christin Rieke, "Computer Vision-Assisted Surgery": Real-Time Instrument Tracking with Machine Learning "http://mediatum.ub.tum.de/doc/1435900/753802.pdf".

(Continued)

*Primary Examiner* — Joel F Brutus
(74) *Attorney, Agent, or Firm* — Ewers IP Law PLLC; Falk Ewers

(57) ABSTRACT

A microscopy system includes a microscope, a stand configured to mount the microscope and including a drive device configured to move the microscope, a detection device configured to detect a spatial position of a target fastened to a body part or to an instrument, wherein the position detection device includes the target with at least one marker element and an image capture device configured to optically capture the target. The microscopy system further includes at least one control device configured to operate the microscopy system according to the detected position of the target, wherein the position detection device is configured to determine the position of the target by evaluating a two-
(Continued)

dimensional image of the image capture device. In addition, a method for operating the microscopy system is provided.

20 Claims, 3 Drawing Sheets

Related U.S. Application Data continuation of application No. 16/393,959, filed on Apr. 25, 2019, now Pat. No. 11,406,455.

(51) Int. Cl.
  *A61B 90/00* (2016.01)
  *G02B 21/00* (2006.01)
  *G06T 7/13* (2017.01)
  *G06T 7/70* (2017.01)
(52) U.S. Cl.
  CPC ........ *G06T 7/70* (2017.01); *A61B 2034/2055* (2016.02); *A61B 2090/3937* (2016.02); *G06T 2207/30204* (2013.01)

(56) References Cited

U.S. PATENT DOCUMENTS

| | | | |
|---|---|---|---|
| 6,675,040 B1 | 1/2004 | Cosman | |
| 6,926,709 B2 | 8/2005 | Bieger et al. | |
| 7,912,532 B2 | 3/2011 | Schmidt et al. | |
| 8,945,149 B2 | 2/2015 | Kim et al. | |
| 9,392,931 B2 | 7/2016 | Urban et al. | |
| 9,827,054 B2 | 11/2017 | Richmond et al. | |
| 10,457,089 B2 | 10/2019 | Wang et al. | |
| 10,575,828 B2 | 3/2020 | Dunlap et al. | |
| 2002/0040190 A1 | 4/2002 | Nagele et al. | |
| 2002/0077544 A1 | 6/2002 | Shahidi | |
| 2004/0150534 A1 | 1/2004 | Bieger | |
| 2007/0073133 A1 | 3/2007 | Schoenefeld | |
| 2007/0265495 A1 | 11/2007 | Vayser | |
| 2010/0279338 A1 | 11/2010 | Halamish et al. | |
| 2011/0015518 A1 | 1/2011 | Schmidt et al. | |
| 2012/0215096 A1 | 8/2012 | Gilboa | |
| 2014/0005487 A1 | 1/2014 | Tesar | |
| 2014/0198197 A1 | 7/2014 | Kaminaga | |
| 2014/0316257 A1 | 10/2014 | Woerlein et al. | |
| 2015/0109427 A1* | 4/2015 | Wood .................. | A61B 6/032 348/68 |
| 2015/0238073 A1* | 8/2015 | Charles .............. | A61B 17/0218 600/102 |
| 2016/0015471 A1 | 1/2016 | Piron et al. | |
| 2016/0035108 A1 | 2/2016 | Yu et al. | |
| 2016/0113728 A1 | 4/2016 | Pion et al. | |
| 2016/0178882 A1 | 6/2016 | Krug et al. | |
| 2016/0202040 A1 | 7/2016 | Schlaudraff et al. | |
| 2016/0228198 A1 | 8/2016 | Hong et al. | |
| 2017/0020627 A1* | 1/2017 | Tesar .................. | A61B 90/361 |
| 2017/0025853 A1 | 1/2017 | Johansson et al. | |
| 2017/0095306 A1 | 4/2017 | Franjic et al. | |
| 2017/0188826 A1 | 7/2017 | Gerlach | |
| 2017/0196641 A1 | 7/2017 | Jagga et al. | |
| 2017/0258531 A1 | 9/2017 | Bodjanski | |
| 2017/0307869 A1* | 10/2017 | Zeng .................. | G02B 21/367 |

FOREIGN PATENT DOCUMENTS

| | | |
|---|---|---|
| CN | 1502089 A | 6/2004 |
| CN | 1918501 A | 2/2007 |
| CN | 101170961 A | 4/2008 |
| CN | 101900875 A | 12/2010 |
| CN | 10258088 A | 7/2012 |
| CN | 103080807 A | 5/2013 |
| CN | 103399413 A | 11/2013 |
| CN | 103892919 A | 7/2014 |
| CN | 10769389 A | 7/2015 |
| CN | 105050527 A | 11/2015 |
| CN | 105717789 A | 6/2016 |
| CN | 106457610 A | 2/2017 |
| CN | 106999256 A | 8/2017 |
| CN | 107438413 A | 12/2017 |
| CN | 107765414 A | 3/2018 |
| CN | 107810400 A | 3/2018 |
| CN | 110398830 A | 11/2019 |
| DE | 3739223 A1 | 6/1989 |
| DE | 19529950 C1 | 11/1996 |
| DE | 10025285 A1 | 12/2001 |
| DE | 102004049258 A1 | 4/2006 |
| DE | 202014103766 U1 | 1/2015 |
| DE | 102014106865 A1 | 11/2015 |
| DE | 102014210056 A1 | 12/2015 |
| DE | 102016217628 A1 | 3/2018 |
| EP | 1193520 B1 | 1/2006 |
| EP | 2296596 B1 | 1/2017 |
| EP | 2082186 B1 | 4/2018 |
| EP | 3508812 B1 | 1/2021 |
| RU | 2462195 C2 | 9/2012 |
| WO | 03105675 A2 | 12/2003 |
| WO | 2008056180 A2 | 5/2008 |
| WO | 2011085815 A1 | 7/2011 |
| WO | 2015094726 A1 | 6/2015 |
| WO | 2016041050 A1 | 3/2016 |
| WO | 2016182611 A1 | 11/2016 |
| WO | 2017049381 A1 | 3/2017 |
| WO | 2017110333 A1 | 6/2017 |
| WO | 2017157763 A1 | 9/2017 |

OTHER PUBLICATIONS

Lepetit, Vincent; FUA, Pascal: Monocular model-based 3D tracking of rigid objects: A survey. In: Foundations and Trends in Computer Graphics and Vision. Bd. 1, 2005, H. 1, S. 1-91. DOI: 10.1561/0600000001.
Article "Electromagnetic Tracking Systems" downloaded at http://www.ndigital.com/products/#electromagnetictracking-systems, 2019.
Article "Optical Measurement" downloaded at http://www.ndigital.com/products/optical-measurement-systems, 2019.
S.Garrido-Jurado et al., "Automatic generation and detection of highly reliable fiducial markers under occlusion"; Pattern Recognition 47 (2014) pp. 2280-2292.
R.A. Boby et al. "Single image based camera calibration and pose estimation of the end-effector of a robot"; 2016 IEEE International Conference.
Petr Oscadal et al. "Improved Pose Estimation of Aruco Tags Using a Novel 3D Placement Strategy"; 2020 Czech Republic.
Chinese Office Action dated Sep. 27, 2024, of Chinese counterpart application No. 202111589545.7, and English language translation thereof.
Chinese Office Action dated Feb. 18, 2024, of Chinese counterpart application No. 202111589545.7, and English language translation thereof.

\* cited by examiner

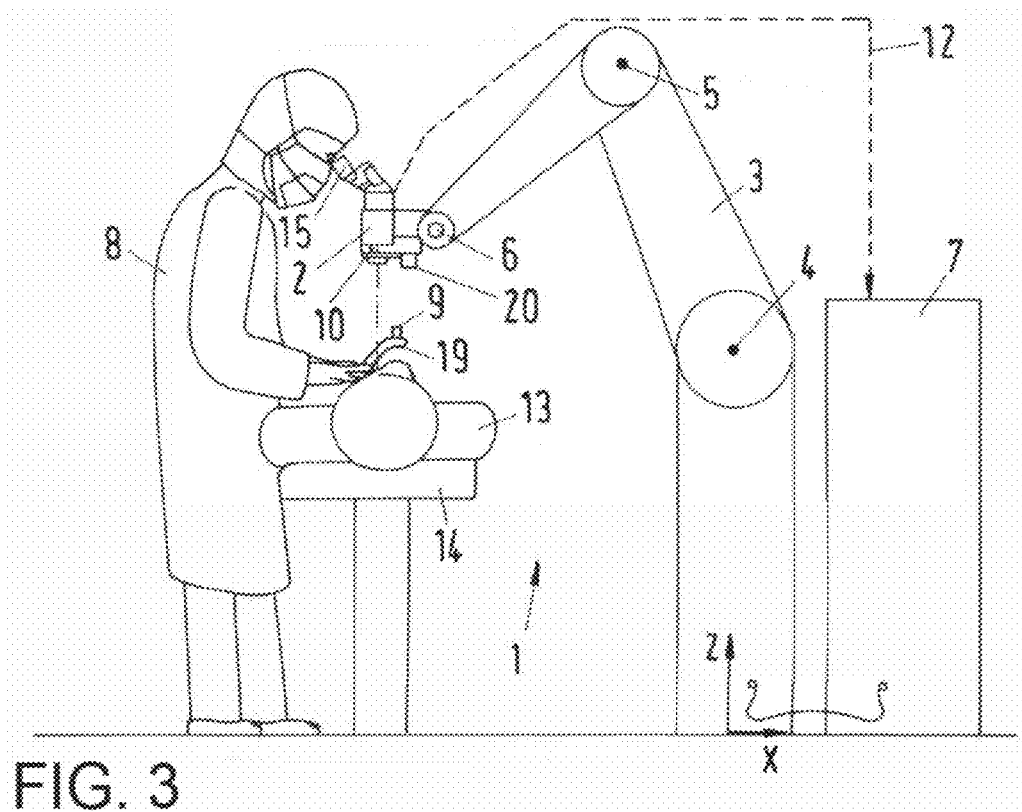
FIG. 3
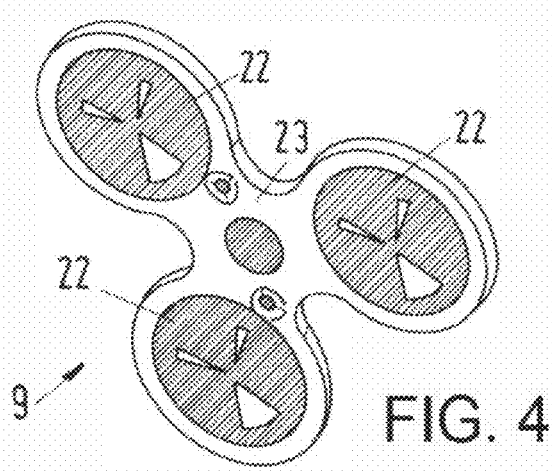
FIG. 4
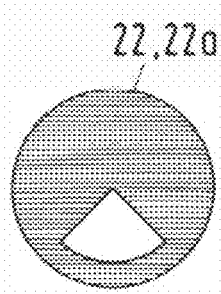 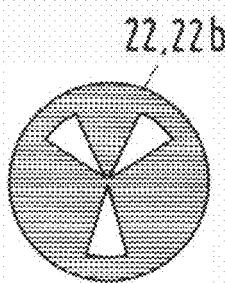 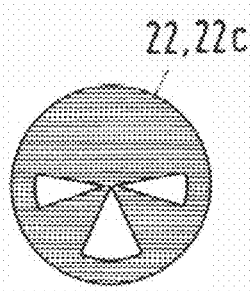 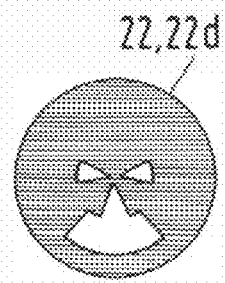
FIG. 5A  FIG. 5B  FIG. 5C  FIG. 5D

MICROSCOPY SYSTEM AND METHOD FOR OPERATING THE MICROSCOPY SYSTEM

CROSS REFERENCE TO RELATED APPLICATIONS

This application is a continuation application of U.S. patent application Ser. No. 17/856,977 filed on Jul. 2, 2022, which is a continuation application of U.S. patent application Ser. No. 16/393,959, filed Apr. 25, 2019, which claims priority to German patent application DE 10 2018 206 406.7, filed Apr. 25, 2018, and the entire content of these applications is incorporated herein by reference.

TECHNICAL FIELD

The disclosure relates to a microscopy system and to a method for operating the microscopy system.

BACKGROUND

Microscopes are often used to provide a magnified view of examination objects. In medical applications, so-called surgical microscopes are used in particular for assisting surgical interventions. Surgical microscopes serve, among other things, to provide a magnified view of regions of a body, in order to give a surgeon better visual orientation during an intervention. These surgical microscopes are generally mounted in a movable manner, in particular on a stand. Among other things, this allows a user to change a position and/or orientation of the microscope, for example in order to modify an angle of viewing onto an examination region or in order to view other examination regions. In many applications, the position is changed by manual actuation of the microscope by the user himself. A disadvantage of this is that the user has to set down instruments that he is using in the intervention, for example, in order to change the position. This takes up time and is not very user friendly.

Foot-operated switches or mouth-operated switches are also known for operating a microscope. However, these are either limited in terms of their use, i.e., they permit only a few degrees of freedom of use, or they are uncomfortable or unhygienic for a user.

DE 10 2014 106 865 A1 describes a method for contactless operation of a surgical microscope. It is known from said document that contactless spatial positioning of the surgical microscope by an operator is possible. The document also describes what is called a three-dimensional sensor, which serves to determine a distance or an orientation. The document does not contain any further explanations concerning this three-dimensional sensor.

US 2017/025853 A1 describes an optical tracking system and optical tracking methods based on passive markers.

WO 2016/041050 discloses a system for tracking a medical apparatus with a collinear arrangement of markers which are arranged at previously known distances from one another on the medical apparatus.

EP 1 193 520 B1 describes a surgical microscope with an objective for observing an object and with a device for detecting the position of object points, wherein the surgical microscope includes a first image sensor and a second image sensor, which are arranged at a distance from each other.

WO 2017/157763 describes a medical tracking method for tracking a spatial position of at least one medical instrument in a medical working space including an anatomical structure of the patient.

SUMMARY

The technical problem to be addressed is to provide a microscopy system and a method for operating a microscopy system, which permit contactless control of the operation of the microscopy system, in particular the tracking of a microscope in up to six spatial degrees of freedom, in an accurate manner and with a small number of components required for this purpose, and therefore also with low manufacturing costs and small installation space requirements.

The technical problem is resolved by providing a microscopy system and a method for operating the microscopy system as described herein.

The microscopy system includes a microscope. Within the meaning of this disclosure, a microscope designates a device for magnified visual observation of an examination object. The microscope can be a classical light microscope, which generates an enlarged image by utilizing optical effects, e.g., by utilizing lenses for beam guidance and/or beam shaping and/or beam deflection. However, the microscope can also be a digital microscope, wherein the image to be viewed by the microscope can be generated by an image capture device and can be presented on a corresponding display device, for example on a display screen.

The microscope can in particular include at least one eyepiece. The eyepiece designates a part of a microscope through which or into which a user looks in order to view the image generated by the microscope. In other words, an eyepiece forms an eye-side optical interface of the microscope. The eyepiece can form a part of a tube. In this case, the microscope can also include the tube. It is possible, for example, that the eyepiece is integrated in the tube, is formed by the tube or can be secured, in particular exchangeably, on a main body of the tube. In the latter case, it is possible for example, for eyepieces with different magnification factors to be secured on the tube.

The tube can in this case include at least one optical element for beam guidance and/or beam shaping and/or beam deflection, e.g., a lens or a prism. However, it is also conceivable that the tube includes no such elements and is configured, for example, as a pipe. This at least one optical element can form an optical path for optical connection of the eyepiece to the microscope. The at least one optical element can, for example, be integrated in the main body of the tube. The tube can also have a mechanical interface for fastening, in particular releasably fastening, to the microscope, in particular to a microscope body. The tube can also have a mechanical interface for fastening, in particular releasably fastening, an eyepiece.

The eyepiece can be connected optically to the objective, in particular via the optical elements discussed herein.

Moreover, the microscope can include at least one objective. This objective can generate a real optical image of an examination object. The objective can in this case include optical elements for beam guidance and/or beam shaping and/or beam deflection.

Moreover, the microscope can include a microscope body. The microscope body can include further optical elements for beam guidance and/or beam shaping and/or beam deflection radiation. It is possible that the objective is secured on the microscope body releasably, i.e., also exchangeably. However, it is also possible that the objective is firmly integrated in or on the microscope body. The objective can in this case be arranged in a fixed position relative to the microscope body. Moreover, the microscope body can have or form at least one fastening interface for fastening, in particular releasably fastening, a tube. It is possible that the microscope body has or forms a plurality of fastening interfaces, in particular two fastening interfaces. This allows different tubes, in particular tubes with different designs, to be fastened to the microscope body. For example, a so-called pivoting tube, a so-called foldable tube, a so-called straight tube or further tubes can be fastened to the microscope body.

It is possible that the eyepiece or the tube with the eyepiece is connected to the microscope body mechanically rigidly and, if appropriate, non-releasably. Moreover, the eyepiece, or the tube with the eyepiece, can be arranged in a fixed position relative to the microscope body. However, as will be explained in more detail below, the eyepiece, or the tube with the eyepiece, is typically likewise fastened releasably, i.e., exchangeably, on the microscope body and/or is movable relative to the microscope body.

The microscopy system moreover includes a stand for mounting the microscope. The microscope, in particular the microscope body, can thus be fastened mechanically to the stand. It is possible that the microscope is fastened to a free end of the stand, in particular movably, e.g., pivotably. The stand is in this case configured in such a way that it permits a movement of the microscope in space, in particular with at least one degree of freedom, typically with six degrees of freedom. It is of course also possible that the stand is configured in such a way that it permits a movement of the microscope in space with a limited number of degrees of freedom, in particular with fewer than six degrees of freedom.

A degree of freedom can in this case be a degree of freedom in translation or in rotation. In particular, a movement with three different degrees of freedom in translation and three different degrees of freedom in rotation can be permitted by the stand.

The degrees of freedom can in this case be related to a reference coordinate system. A vertical axis (z axis) of this reference coordinate system can be oriented parallel to the gravitational force and counter to the latter. A longitudinal axis (x axis) of the reference coordinate system and a transverse axis (y axis) of the reference coordinate system can span a plane which is oriented perpendicularly with respect to the vertical axis. Moreover, the longitudinal axis and the transverse axis can also be oriented orthogonally with respect to each other. Thus, the reference coordinate system can be a Cartesian coordinate system.

Moreover, the stand includes at least one drive device configured to move the microscope. The stand typically includes a plurality of drive devices. A drive device designates a device for generating a driving force or a driving moment. Such a drive device can be a servo motor, for example. Of course, the stand can also include means for transmitting forces or moments, e.g., gear units. In particular, it is possible for the at least one drive device to be actuated in such a way that the microscope executes a desired movement and thus a desired change of position in space or adopts a desired position and/or orientation. It is in this case possible that a speed of movement is limited to a predetermined maximum speed. It is moreover possible that an extent of the working space of the stand is limited.

For example, the at least one drive device can be actuated in such a way that an optical axis of the objective adopts a desired orientation. Moreover, the at least one drive device can be actuated in such a way that a reference point of the microscope, e.g., a focal point, is located at a desired position in space.

A desired position can in this case be predefined by a user or by another superordinate system. Methods for controlling the at least one drive device according to a desired position and according to a kinematic structure of the stand are known to a person skilled in the art. The user can in this case be a person who operates the microscope, in particular who looks into/through the eyepiece in order to obtain a magnified view of the object. It is possible that the microscope is what is called a surgical microscope. In this case, the user can in particular be a surgeon.

The microscopy system moreover includes at least one position detection device configured to detect a position of at least one target. The position detection device includes the at least one target, wherein the latter includes or has at least one marker element. It is possible that the target includes precisely one marker element or two or more marker elements. The target typically includes three marker elements. The marker elements can in this case be arranged in a fixed position relative to one another. A relative position between the marker elements may be known in advance. The marker elements may not in this case be in a collinear arrangement. It is conceivable that a target includes a support body, wherein the at least one marker element is fastened to the support body. A marker element can in this case be one that is optically detectable and thus also detectable in the image, in particular an optically detectable pattern.

The marker element is typically a passive marker element. A passive marker can in particular be a marker that does not consume any energy in order to be optically detectable or reliably optically detectable. Thus, a passive marker also does not have to be supplied with energy, e.g., from an energy storage device such as a battery or from a mains network. This in turn permits a construction with minimal installation space requirements.

In particular, a passive marker cannot generate a signal, and in particular cannot emit a signal that is received by a receiving device, in particular by the image capture device. In particular, passive markers do not therefore require any energy in order to permit detectability by the image capture device. In this way, energy consumption can advantageously be minimized during operation of the microscopy system. However, in an exemplary embodiment, a marker element may also be an active marker element.

It is moreover possible that the at least one marker element is a non-reflecting marker element and/or a non-phosphorescent marker element and/or a non-fluorescent marker element.

The position detection device moreover includes an image capture device, in particular precisely one image capture device, for optical acquisition of the target and therefore also of the at least one marker element. The image capture device can in this case be a camera, for example a charge-coupled device (CCD) camera or a complementary metal-oxide semiconductor (CMOS) camera. It is of course possible that the image capture device also includes an objective that serves to image objects in an acquisition range of this image capture device. The acquisition range can designate a field of view of the image capture device.

The target and the image capture device thus form elements of the position detection device.

An element of the position detection device, typically the target, can in this case be arranged near the patient. This can mean that the element can be arranged in a half-space delimited by a plane which is oriented perpendicularly with respect to an optical axis of the microscope and which extends through a point of intersection between the optical axis and an optical or transparent element of the microscope and, along the optical axis, is arranged behind this plane. When the microscope is oriented towards a patient, the optical axis is oriented from the microscope towards the patient, and the patient is also arranged in this half-space.

In particular, the element is fastened or fastenable to a body part of the user, to an instrument, to a patient or to an item of operating theatre equipment.

The instrument can in particular be a medical instrument, more particularly a surgical instrument. For example, this includes instruments such as clamps, holders, syringes, tweezers, spatulas, scissors, scalpels, wound hooks, forceps, aspirators, cauterizing tools, but also retractors, e.g., a brain retractor. The instrument can in particular be an instrument that can be guided by a user's hand. An item of equipment in an operating theatre can be, for example, an operating table or a Mayfield clamp.

The element of the position detection device can be fastened, for example by a corresponding retaining device, to a body part of the user, to an instrument, to a patient or to an item of operating theatre equipment. A person skilled in the art will be aware in this context that this fastening can be produced in different ways.

The element of the image capture device here can in particular be fastened on, and fixed in position relative to, the body part, the instrument, the patient or the item of operating theatre equipment. The position can in this case be detected in a coordinate system of the position detection device. It is then possible for the position in the coordinate system to be converted into a position in the reference coordinate system explained above. It is thus possible, for example, that a geometric transformation from the coordinate system of the position detection device into the reference coordinate system is previously known. This can be determined, for example, by so-called registration.

Moreover, the remaining element of the position detection device, i.e., the target, or typically the image capture device, is arranged on the microscope. It is conceivable here that the remaining element is connected mechanically rigidly to the microscope, in particular to part of the microscope. In other words, the remaining element can be fastened to a part of the microscope so as to be fixed in position relative to said part of the microscope. For example, the remaining element can be connected mechanically to the eyepiece or to the tube. The remaining element can also be connected to the microscope body.

Moreover, it is conceivable to use fluorescent or phosphorescent marker elements. organic light-emitting diode (OLED) marker elements, which light up autonomously, are also conceivable.

Particularly if the image capture device is arranged on the microscope, an acquisition range of the microscope can at least partially overlap the acquisition range of the image capture device for optical acquisition of the target. It is also possible that the acquisition range of the image capture device is arranged completely within the acquisition range of the microscope or that the acquisition range of the microscope is arranged completely within the acquisition range of the image capture device. The image capture device for optical acquisition of the target can be arranged accordingly on the microscope, in particular on a microscope body. Moreover, the image capture device for optical acquisition of the target may be different from an image capture device of the microscope. The image capture device of the microscope can serve, for example, to image objects in the acquisition range of the microscope and then to display these images (enlarged) on a corresponding display device.

In other words, the microscopy system can include at least two different image capture devices, namely, on the one hand, the image capture device of the microscope and, on the other hand, the image capture device for optical acquisition of the target.

The image capture device for position detection can in particular be configured and/or arranged in such a way that, with a working distance of at least 200 millimeters (mm), it is possible to image an object located in this working distance, in particular along the optical axis of the microscope, with a diameter of at least 250 mm or at least 300 mm. Moreover, the image capture device of the position detection device can in particular be arranged and/or configured in such a way that a marker element at a working distance of at most 600 mm is imaged into a partial region of the image with a predetermined minimum size. The minimum size can be, for example, 10, 50 or 100 pixels.

It is possible, but not essential, that an element of the position detection device, in particular the image capture device of the position detection device, is arranged in a fixed position relative to the eyepiece. In particular, the element can be connected mechanically to the eyepiece. However, the element of the position detection device is typically arranged in or on the microscope body, in particular in a housing of the microscope body, wherein optical elements for beam guidance and/or beam shaping and/or beam deflection can also be arranged in this housing.

It is moreover possible that the position detection device serves to detect the position of the target relative to the image capture device. In other words, a relative position between target and image capture device can thus be determined, wherein this relative position is used to calculate the position of the target and/or of the image capture device in the reference coordinate system.

For the position detection, a target, in particular the at least one marker element of the target, depicted in the image can be detected in the image in an image-based manner, i.e., by image evaluation, wherein the relative position between target and image capture device can then be determined according to the position of the target in the image coordinate system, i.e., according to the target's image position. For this purpose, the image capture device can be suitably calibrated. It is of course possible that a plurality of targets are imaged, i.e., are detected simultaneously. In this case, it is possible to differentiate between said plurality of targets and to determine their positions. A resulting position can then be determined on the basis of said plurality of positions.

If an element of the position detection device, e.g., the target, can be fastened to a body part of the user, to an instrument, to a patient or to an item of operating theatre equipment, then it can also be spatially fixed in position relative to the body part of the user, to the instrument, to the patient or to the item of operating theatre equipment. In this case, from the position of the element, it is possible to determine the position of the body part of the user, of the instrument, of the patient or of the item of operating theatre equipment, in particular the position of a corresponding reference point. The position of the reference point relative to the element of the position detection device may in this case be known in advance and may in particular be determined by a suitable calibration. However, this is not essential, since only the position of the target, not necessarily the position of the body part, is detected for control purposes. In particular when activating a corresponding operating mode, it can thus be assumed that the target is located in a desired relative position relative to the body part. It can moreover be assumed that the relative position between body part and target does not change in normal operation.

In other words, from the relative position between target and image capture device, it is also possible to determine the position of the body part of the user, of the instrument, of the patient or of the item of operating theatre equipment, in particular in the reference coordinate system. For example, the element of the position detection device can be fastened to the holder device for holding/fastening to a body part of the user. Such a holding device can be, for example, a glove or other holding device. The element of the position detection device can also be fastened to the holder device for holding/fastening to an instrument. Such a holding device can be, for example, a clamp holder.

The at least one image capture device is typically fastened to the microscope or to a part thereof in such a way that the body part of the user, in particular his hand, or an instrument guided by the user, the patient or the item of operating theatre equipment (and thus also a target fastened thereto) is located in an acquisition range of the image capture device when the body part of the user, the instrument, the patient or the item of operating theatre equipment is located in the acquisition range of the microscope during the intended use of the microscope.

Of course, the device for position detection also permits the determination of a change of position of the target and therefore also of the body part/instrument/patient/item of operating theatre equipment. The position and/or change of position can be determined here by the position detection device itself or by an evaluation device connected thereto by a signal link and/or data link. This evaluation device can likewise be part of the microscopy system. The evaluation device can be a computing device, e.g., a computing device configured as a microcontroller.

The microscopy system moreover includes at least one control device configured to control the operation of the microscopy system on the basis of the detected position of the target and thus also on the basis of the position of the body part/instrument/patient/item of operating theatre equipment. The control device can form the evaluation device for determining the change of position. The position detection device can be connected to the control device by a signal link and/or data link. In other words, the microscopy system can be controlled in a position-based manner. This in turn advantageously permits contactless control of the microscopy system.

The control device can in particular be a control device for controlling the at least one drive device according to the detected position, in particular according to the determined change of position, of the target. In other words, the control device can generate control signals for the at least one drive device according to the detected position of the target, wherein these control signals can then be transferred to the drive device. For example, a desired movement parameter for the movement of the microscope can be determined according to the detected position or change of position of the target. A movement parameter can in this case be a desired position, a desired change of position, a desired direction of movement, a desired speed or a desired acceleration, a maximum admissible speed of movement, a maximum admissible acceleration or a further movement parameter.

It is possible in particular that the control device actuates the at least one drive device according to the detected position of the target, in such a way that the microscope tracks a movement of the target. This can in particular mean that a change of position of the target is determined, wherein the microscope executes the same change of position or a scaled change of position.

Alternatively or in addition, the control device can be a control device for adjusting, in particular changing, an operating parameter and/or a movement parameter and/or an operating mode of the microscope according to the detected position, in particular according to the determined change of position, of the target. An operating parameter of the microscopy system can be, for example, a desired magnification, a focal position, a zoom factor, an illumination intensity or a further operating parameter. Examples of movement parameters have already been explained above. In particular, a maximum admissible speed of movement can be set, for example. Examples of operating modes are explained in more detail below. An operating mode can also be a viewing mode or an operating mode.

The control device may be configured in particular as a computing device, e.g., as a microcontroller, or may include such a computing device.

According to an aspect of the disclosure, the position detection device is configured to determine the position of the target by evaluating a two-dimensional image generated by the image capture device of the position detection device. In particular, a spatial setting, i.e., a three-dimensional position and a three-dimensional orientation, can be determined by an evaluation of a two-dimensional image, in particular of precisely one two-dimensional image, by the position detection device. This may also be referred to as so-called monoscopic position detection. In particular, an evaluation of intensity values of pixels (image points) of the two-dimensional image can be carried out in order to determine the position.

An example of a method for detecting the position of a target or of a marker element by evaluation of (precisely) one two-dimensional image of an image capture device is described, for example, in US 2017/258531 A1 mentioned in the introduction.

The latter method advantageously results in precise and rapid detection of the position of a target using a small number of components, in particular only one image capture device, and with reduced computing power, since only one two-dimensional image has to be evaluated for the position detection. This in turn advantageously permits reduction of the costs of manufacturing the proposed microscopy system and reduction of the installation space requirements of a microscopy system with a position detection function, particularly by comparison with stereoscopic position detection devices, which require at least two image capture devices.

It is thus possible, by the image capture device, to detect a target fastened to an instrument, for example a surgical instrument, e.g., an aspirator or a pointer. It is thus possible to determine the spatial position of the target, and also that of the aspirator, and in particular also changes of this spatial position. It is also possible to detect a target fastened to a body part of a user, for example of a surgeon. For example, the target can be fastened to a hand, a glove or a forearm of the user. In this way, it is possible to detect a position and changes of the position of the target and therefore also of the body part. Conversely, however, it is also possible, by an image capture device fastened to the instrument or to the body part of the user, to detect a target arranged on the microscope and thus to determine a spatial relative position.

This in turn advantageously permits control of the operation of the microscope, and in particular of a spatial movement of the microscope, according to the detected position, in particular the detected change of position. In particular, the microscope can be controlled, in a position-tracking mode, in such a way that it executes the same changes of position as the target.

Overall, a microscopy system is advantageously obtained with which an operation of the microscopy system, in particular a movement of the microscope and/or the adjustment of operating parameters of the microscope, can be controlled reliably, precisely and rapidly on the basis of the movements of a body part, in particular a hand, of a user, an instrument moved by the user, an position or change of position of a patient, or a position or change of position of an item of operating theatre equipment. In particular, contactless control is permitted, which makes operation of the microscope more comfortable and reduces the time lost during operation, in particular during positioning, and can also further reduce a risk of infection of the patient in the case of manual control of the microscopy system. In particular, there is the possibility of controlling the microscopy system with the aid of hand movements or instrument movements. This in turn advantageously permits easy repositioning of the microscope, for example in order to permit viewing of another region that is to be treated, in order to improve a user's perception of depth, in order to react to a repositioning of the patient relative to the microscope, or in order to compensate for a movement of the site, e.g., by brain shift or respiration. However, it is not only the movement of the microscopy system that can be controlled: further operating parameters of the microscopy system, for example a zoom, can also be easily adjusted without taking up an undesirable amount of time.

In a further exemplary embodiment, the control device is a control device for controlling the at least one drive device according to the detected position of the target and/or a control device for adjusting at least one operating parameter and/or movement parameter and/or for adjusting an operating mode of the microscope. This has already been explained above.

In a further exemplary embodiment, the image capture device of the position detection device is arranged in or on the microscope in such a way that beams detected by the image capture device run through at least one optical element of the microscope. An optical element of the microscope can in particular be an element for beam guidance and/or beam shaping and/or beam deflection. The optical element of the microscope designates an element which is used to provide a view, in particular a magnified view, through the microscope. In particular, an optical element can be a lens. It is thus possible that objects in the acquisition range of the image capture device of the position detection device are shown in an enlarged or reduced form through an optical element of the microscope. For example, the image capture device can for this purpose be arranged in a housing of the microscope, in particular in a housing of the microscope body, wherein at least one optical element of the microscope is arranged between the image capture device of the position detection device and the acquisition range to be imaged. This advantageously permits a further reduction in the number of components required for reliable position detection, since it is possible to make use of elements of the microscope that are already present. Likewise, the position detection function is thus incorporated into the microscopy system in a manner that requires little installation space.

It is possible in this case that beams detected by the image capture device additionally run through at least one optical element which is not an optical element of the microscope, i.e., which does not serve for viewing through the microscope. In particular, such an optical element can be part of an optical system of the image capture device of the position detection device.

In another exemplary embodiment, the image capture device of the position detection device is arranged in or on the microscope in such a way that beams detected by the image capture device do not run through at least one optical element of the microscope. In this context too, the optical element can be an element for beam guidance and/or beam shaping and/or beam deflection. In particular, no optical element of the microscope is therefore arranged between the image capture device of the position detection device and the acquisition range to be imaged.

However, this exemplary embodiment can include an arrangement of the image capture device in or on the microscope in such a way that beams detected by the image capture device run through at least one transparent element of the microscope that does not serve for beam guidance and/or beam shaping and/or beam deflection. By way of example, such an element can be a glass plate. The transparent element can be arranged in or on the microscope, in particular in or on the microscope body.

However, it is also possible in this case that beams detected by the image capture device additionally run through at least one optical element which is not an optical element of the microscope, i.e., which does not serve for viewing through the microscope. In particular, such an optical element can be part of an optical system of the image capture device of the position detection device.

In this way, the image capture device is advantageously protected from dirt and moisture, and this additional image capture device is at the same time easily integrated in the microscopy system since optical parameters of the image capture device do not have to be adapted to the optical properties of optical elements of the microscope.

In a further exemplary embodiment, a transparent element of the microscope is arranged between the image capture device of the position detection device and the acquisition range to be imaged. In other words, in the beam direction from an object to be imaged to the microscope, the image capture device can be arranged behind a transparent cover element of the microscope. The corresponding advantages have already been explained above.

In a further exemplary embodiment, the position detection or the position determination can be carried out according to a sequence of at least two images, or precisely two images, typically according to a sequence of precisely or at least three images. The images are in this case two-dimensional images which are generated chronologically at different time points, in particular chronologically one after another or immediately after one another, by the same image capture device. Typically, the images of the sequence are taken within one (short) time period, for example at a time interval of no longer than one microsecond or no longer than one millisecond. Moreover, a time interval between images generated chronologically one after another or images generated immediately after one another can be, for example, in a range from 10 milliseconds (ms) to 35 ms. However, it should be noted that this time interval depends on a desired exposure time in the generation of an image and may therefore be dependent on the sensor size and other boundary parameters.

In particular, one or more marker elements can be detected on an image basis in each of the images, and, for each image, an image-specific position can thus be determined in an image coordinate system. A resulting position of a marker element in an image coordinate system, which is then evaluated to determine the position of the target, is defined on the basis of the image-specific positions, e.g., by a notification or other suitable data fusion method. Since it may be assumed that the position of the marker elements has not changed, or has changed by not more than a predetermined extent, in the period of time of generation of the sequence, the precision of the position detection is also not influenced, or is influenced by not more than a predetermined extent.

This has the advantage that the precision of the position detection can be ensured even in the case of exposure conditions that are not favorable for position detection.

Thus, for example, an acquisition region of the microscope can be illuminated in such a way that it includes different illumination regions, i.e., regions with different illumination intensities. For example, a first illumination region can be an illumination cone, which is illuminated with an illumination intensity above a first predetermined threshold value. A second illumination region can be a region outside this first illumination region and is illuminated with an illumination intensity below a further predetermined threshold value. A third illumination region can be a transition region between the first transition region and the second transition region. The target, in particular marker elements of the target, can be arranged in these different illumination regions. In particular, it is possible that different marker elements of a target are arranged in different illumination regions. However, this makes it difficult to evaluate an individual image in order to determine the position. In particular, in such a scenario, the choice of certain image capture parameters, for example an illumination time, an aperture stop and further imaging parameters, can have the effect that certain marker elements, on account of overexposure or underexposure, are not detectable, or are detectable only with difficulty, on an image basis. This can have the effect, for example, that in the transition region an identification of marker elements in the image, which identification can be based, e.g., on an edge detection and edge extraction, is made difficult by the intensity profiles influenced on account of the illumination.

It is also possible to capture the different images of the sequence with different image capture parameters and/or with different illumination parameters.

By choosing different image capture parameters and/or illumination parameters for capturing of the individual images of the sequence, it may then be possible to reliably identify marker elements in the different illumination regions explained above and to use the corresponding information for position determination.

In a further exemplary embodiment, the sequence can be captured by utilizing a high dynamic range (HDR) imaging technique. This means that the images are so-called HDR images. This also advantageously permits improved reliability of the image-based identification of marker elements, in particular in different illumination regions.

In a further exemplary embodiment, the target includes a marker element, wherein the marker element has an elliptical marker body or an elliptical marker surface and a geometric center of this marker body or of this marker surface. Here, the term "elliptical" also includes a circular configuration.

The marker body or the marker surface, which can also be designated as inner marker body or inner marker surface, is filled with color spectrum points, which are distributed radially with respect to the geometric center. A color value of each color spectrum point of the marker body/marker surface is defined, and can thus be determined, according to an angle between a horizontal line through the geometric center and a further line through the geometric center and the corresponding color spectrum point. In other words, an assignment, in particular an unambiguous assignment, e.g., a functional relationship, may exist between the color spectrum value and the angle and the distance of the color spectrum point from the geometric center. The angle and distance can be given in the form of polar coordinates.

If at least two such marker elements, in particular of one target, are depicted in the image, then, in a further method step, edges of these at least two marker elements, in particular of the marker bodies or marker surfaces, can be detected on an image basis. In a further method step, blobs in the quantity of the detected images can be detected. In this context, blobs can designate continuous regions in the image.

Moreover, ellipses can be detected in the quantity of the detected blobs. In a further method step, sinusoidal patterns in each detected ellipse can be evaluated. Moreover, on the basis of this evaluation, a two-dimensional position of the at least two marker elements can be determined, and then a three-dimensional position can be determined on the basis of the two-dimensional dimensions.

In the necessary steps for detection, in particular of edges, blobs, ellipses and sinusoidal patterns, image processing methods that are known to a person skilled in the art may be applied.

Such a determination of the three-dimensional position is described in US 2017/025853 A1 discussed in the introduction, and reference is made in full to the corresponding disclosure. In other words, the disclosure content of US 2017/025853 A1 is incorporated in its entirety herein by reference.

This results in simple, reliable and precise position detection that does not require great outlay in computing terms.

In a further exemplary embodiment, the position-based control can be carried out in real time. This can mean that a control signal dependent on the detected position, and used for controlling the operation, is generated in a period of less than 100 ms or 10 ms or 1 ms after detection of the position of the target, or a process induced by such a control signal is carried out or completed in a period of less than 100 ms or 10 ms or 1 ms after detection of the position of the target. This permits a temporally fast, position-based control.

In a further exemplary embodiment, the microscopy system includes at least one illumination device for illuminating the target. In particular, the position detection device can include the at least one illumination device. The illumination device can in this case be mechanically connected to the stand or to the microscope. For example, it is possible that the illumination device is arranged on and fixed in position relative to the eyepiece or arranged on and fixed in position relative to the microscope body. It is possible, for example, that the illumination device is arranged in a fixed position relative to the image capture device. Thus, the illumination device can also be fastened on the image capture device, for example.

The illumination device is typically configured and/or arranged in such a way that the target is arranged in the illumination range of the illumination device when the microscopy system is used in the manner intended. In particular, the illumination device can be configured and/or arranged in such a way that the illumination range of this device and the acquisition range of the image capture device of the position detection device completely or at least partially overlap.

The illumination device can in particular include at least one light-emitting diode (LED). Typically, the wavelength of the radiation emitted by the illumination device differs from wavelengths of other devices in the environment of the microscopy system, for example in the operating theatre.

In this way, the reliability of an image-based detection of the target is enhanced, in particular in operating scenarios in which only a little ambient light is available. In particular, reliable optical detection of the target can be ensured even in illumination scenarios in which there is little available light with wavelengths from the visible range, for example in darkened operating theatres.

In a further exemplary embodiment, the illumination device generates light with a wavelength outside the visible (wavelength) range. Typically, the illumination device generates light with a wavelength from the infrared range. It is possible in this case that the illumination device does not generate any light with a wavelength from the visible range. However, it is also possible that the illumination device generates both light with a wavelength from the visible range and also light with a wavelength outside the visible range. For example, the illumination device can generate light in a wavelength range of 780 nanometers (nm) (inclusive or exclusive) to 1 mm (inclusive or exclusive).

The advantage of this is that the optical detection of the marker elements is not disturbed by light in the visible range, which light can change in different illumination scenarios in the environment of the microscopy system. For example, the aforementioned reliability of the optical detection can be ensured without a user of the microscopy system or a further person being disturbed by visible light of the illumination device.

In a further exemplary embodiment, the intensity of the illumination is adjustable depending on the distance of the target from the image capture device. The distance can be determined, for example, depending on the detected position of the target, in other words the relative position between image capture device and target. In particular, an image generated by the image capture device can thus be used to determine the distance of a target, or of a marker element of the target, from the image capture device. For example, the intensity of the illumination can be increased in proportion to the distance. Of course, other functional or predefined relationships between distance and intensity of illumination are conceivable, for example in the form of an allocation. This advantageously permits reliable detection of the target by the image capture device for different distances between target and image capture device.

Alternatively or in addition, a working distance, e.g., in the form of a focal position, of the image capture device is adjustable on the basis of the distance of the target from the image capture device, which can also be designated as the target distance. In particular, the working distance can be adjusted proportionally to the target distance in such a way that, as the target distance increases, the detection range of the image capture device becomes smaller. The working distance typically tracks the target distance. This may mean that, when the target distance changes, the working distance is also changed, e.g., proportionally or in inverse proportion. In particular, the change takes place in such a way that the target, despite limited depth of definition of the image capture device, can be sharply imaged. The working distance can in this case be changed electronically or by modification of the optical path, i.e., of optical elements for beam guidance and/or beam shaping. In this way too, the reliability of the detection of the target is improved.

Alternatively or in addition, an exposure time of the image capture device is moreover adjustable depending on the target distance. In particular, the exposure time can be adjusted in proportion to or in potential dependency on, e.g. with an exponent of 2 or 4, the target distance, in such a way that as the target distance increases, the exposure time is also extended. In this way too, the reliability of the detection of the target is advantageously improved.

In a further exemplary embodiment, the microscopy system includes at least one filter for filtering the radiation generated by the image capture device, i.e., the radiation used to generate the image. The filter can be a spectral filter, for example. The filter can be transparent for light from the infrared wavelength range and not transparent, or less transparent, for light with wavelengths outside the infrared wavelength range. The filter thus filters the radiation that is then used to generate the image of the image capture device. The filter can in this case be fastened to the microscope, in particular to the microscope body or to the eyepiece, or to the image capture device.

Alternatively or in addition, the image capture device configured to generate the image captures only radiation of a defined wavelength or of a predetermined wavelength range, in particular of the aforementioned infrared wavelength range. In this case, for example, a sensor of the image capture device can be configured in such a way that it captures only light of the predetermined wavelength range and then generates the image on the basis of this captured radiation.

Alternatively or in addition, the image capture device is a monochrome image capture device. The latter can generate intensity images, in particular grey-scale images, on the basis of radiation with wavelengths from a large wavelength range, in particular all detectable wavelengths. This advantageously has the effect that, compared to color cameras for the sensor of the image capture device, more radiation power can be utilized to generate the image and the latter is therefore more sensitive to changes of intensity. Moreover, in this case the sensor of the image capture device can be configured with a smaller surface area than when a color camera is used, and this reduces the manufacturing costs.

This permits, in particular in connection with the aforementioned illumination device, a further improvement in the reliability of detection of the target, since changing light intensities in the visible range do not influence the reliability of the detection and therefore the position detection. Moreover, this results in simplified data processing for evaluation of the images generated.

In a further exemplary embodiment, the microscopy system includes a means for activating a position-based control of the microscopy system. The means for activating the position-based control can therefore also be a means for activating the contactless control of the microscopy system. The activating means can include an interface for input of an activation signal by the user. For example, the input can be made by an actuation, for example by a foot or a hand. Thus, the microscopy system can, for example, include a hand-actuated or foot-actuated switch. A mouth-operated switch is also conceivable for the activation. An acoustic input is also conceivable, for example in the form of a voice command. In this case, the activating means can comprise a microphone. Of course, other exemplary embodiments of the activating means are also conceivable.

When the activating means is actuated, the microscopy system is set to a state in which it is controllable on a position basis. In this state, the position-based control explained above takes place.

Of course, the microscopy system can also include a means for deactivating the position-based control. This deactivating means can form the activating means or can also be configured separate from the latter. When the deactivating means is actuated, the microscopy system is set to a state in which it is not controllable on a position basis. In the state not controllable on a position basis, the position of the target is not used to control the microscopy system. However, the position information can of course be used for other applications, e.g., for spatially correct presentation of an instrument in a virtual image of the site.

This has the effect that the microscopy system can be operated in different operating modes, as a result of which a spectrum of use is broadened.

In a further exemplary embodiment, the image capture device is a wide-angle camera. A wide-angle camera can in this case designate a combination of camera and wide-angle objective. A wide-angle camera can in this case have a field angle which is greater than a field angle of 50° (exclusive), in particular at focal distances in the range of between 28 mm (inclusive) and 38 mm (inclusive). It should be noted here that other focal distances can also be chosen.

In particular, the field angle of a wide-angle camera is greater than that of a camera with a normal-angle objective which has a field angle in the range of approximately 40° to 50° and whose imaging at best corresponds to the perspective perception of humans. Moreover a focal length of a wide-angle camera can be shorter than a focal length of a camera with a normal-angle objective. Remote objects are imaged smaller by a wide-angle camera. Thus, in particular, a wide-angle camera reduces the image scale with the same motif distance. Furthermore, the depth of field that is characteristic of wide-angle photos is also obtained. A wide-angle objective thus has the opposite properties of the tele-objective. The wide-angle objectives likewise include the fisheye objectives.

This advantageously permits an improved detection of the position of the target and in particular of the distance of the marker from the image capture device along an optical axis of the image capture device. It may in fact be assumed that, as the field angle of the image capture device increases, the size of the imaged marker also changes more strongly in the event of changes of distance, which can be utilized for more precise determination of the distance. A further advantage is that objects arranged very close to the image capture device can also be reliably captured. This is advantageous since a target may generally be arranged near the image capture device.

In a further exemplary embodiment, an identity, in particular an unambiguous identity, is assigned to the marker element, wherein this identity is identifiable on an image basis. An image-based identification may in this case signify the determination of the identity by evaluation of the image data. In this way, different marker elements can be differentiated from one another. This in turn broadens a spectrum of use of the microscopy system by using marker elements with such different identities that can be determined on an image basis. Examples of uses are explained in more detail below.

In a further exemplary embodiment, an operation of the microscopy system is controllable on the basis of the identified identity. For example, at least one of the operating parameters of the microscopy system that have already been discussed above can be adjusted depending on the identity, e.g., adjusted to a predetermined value. Alternatively or in addition, at least one of the movement parameters of the microscopy system that have been discussed above can be adjusted depending on the identity, e.g., adjusted to a predetermined value.

Thus, for example, a correlation may exist between identity and the at least one adjustable operating parameter and/or movement parameter. This correlation can be given for example in the form of a user profile, which is assigned to a predetermined identity of a marker element and which, for example, can be generated by a user input. Parameters corresponding to the preferences of a user can be stored in this user profile and are adjusted after identification of the corresponding marker element. With just a few inputs by the user, this advantageously permits comfortable adjustment of parameters, and therefore an improved operation of the microscopy system.

Alternatively, a predetermined operating mode or a plurality of predetermined operating modes can be activated only if a marker element with a predetermined identity is identified. For example, a position-tracking mode can be activated only when a corresponding marker element is identified. Thus, for example, a correlation may exist between identity and the at least one operating mode that is to be activated.

Moreover, an overall operation of the microscopy system, e.g., also including the magnified view, can be activated only when a corresponding marker element is identified.

This advantageously permits the prevention of unauthorized use of the microscopy system or of predetermined operating modes or even provides a kind of protection against theft. Overall, this therefore improves the operating safety of the microscopy system.

Moreover, it is alternatively possible that predetermined identities of marker elements are assigned to different users, e.g., surgeons. The identity of an identified marker element can then be stored, in particular in connection with a time period of the identification. In turn, this makes it possible to keep a record of the use of the microscopy system by one or more users. For example, it is possible subsequently to ascertain which surgeon has used the microscopy system and at what time.

A further exemplary embodiment includes open-loop or closed-loop control of the movement of the microscope according to at least one operating parameter of the microscope. Alternatively or in addition, an exemplary embodiment includes open-loop or closed-loop control of the movement of the microscope according to at least one operating parameter of the image capture device of the position detection device.

This may mean that at least one movement parameter of the microscope is adjusted on the basis of one or more operating parameters of the microscope and/or of the image capture device. In this case, movement parameters can be differentiated from the operating parameters. However, it is also conceivable that a parameter forms both a movement parameter and also an operating parameter. For example, a correlation or another previously known relationship, e.g., a functional correlation, may exist between different operating parameters or operating parameter quantities and a movement parameter or a movement parameter quantity, wherein this correlation or this relationship is utilized to adjust the movement parameters. Of course, other parameters of the open-loop or closed-loop control, for example controller parameters, limit values or other parameters of the movement, can also be adjusted on the basis of at least one operating parameter of the microscope.

An operating parameter of the microscope have already been explained above. An operating parameter of the image capture device is, for example, an adjustable working distance of the image capture device. An operating parameter of the eyepiece or of the tube is, for example, a relative position between eyepiece and microscope body.

For example, a speed, in particular a maximum speed or a maximum admissible speed of the movement can be adjusted on the basis of a currently adjusted magnification of the microscope. In particular, the maximum speed or the maximum admissible speed of a movement can decrease in proportion to the increase in magnification.

This advantageously permits enhanced operating safety and improved user-friendliness of the operation of the microscopy system.

In a further exemplary embodiment, a number of the degrees of freedom enabled for the movement of the microscope is adjustable. For example, one, two, three, four, five, or six degrees of freedom of the movement of the microscope can be enabled. Alternatively, but typically in addition, a nature of the enabled degrees of freedom is adjustable. For example, a selected degree of freedom of translation and/or a selected degree of freedom of rotation can be enabled. If such a degree of freedom is enabled, the movement of the microscope is possible with such a degree of freedom. It is possible that only degrees of freedom of rotation or only degrees of freedom of translation are enabled.

Moreover, it is possible that a coordinate system specific to the degree of freedom is also adjustable, wherein the number of the degrees of freedom enabled for the movement of the microscope is adjustable with respect to or relative to this coordinate system. The coordinate system specific to the degree of freedom can in particular be the reference coordinate system explained above or a coordinate system with a fixed focal point. Of course, other coordinate systems can also be used.

In the case of a coordinate system with a fixed focal point, an origin of the coordinate system can lie at the focal point. A vertical axis can extend along the optical axis of the microscope. The two remaining axes can span a plane and can each be oriented perpendicularly with respect to the vertical axis and to each other. In this case, for example, a so-called point lock operation is possible, wherein the position of the focal point in the reference coordinate system is fixed, and only the degrees of freedom required for the rotation about the axes of the coordinate system with fixed focal point are enabled. In this case, the degrees of freedom do not have to coincide with degrees of freedom provided mechanically by the stand, and they can therefore also be designated as virtual degrees of freedom. It is therefore conceivable that only two virtual degrees of freedom are enabled for a movement, while a movement of the stand nonetheless takes place about all degrees of freedom possible for the stand.

It is possible in this case that the number and/or the type of the enabled degrees of freedom are adjusted on the basis of the detected position. For example, it is conceivable that a predetermined movement is carried out by the target, wherein this movement is detected by the position detection, and the number and/or type, assigned to this movement, of degrees of freedom to be enabled is then enabled. Moreover, depending on the position, a predetermined operating mode of the microscopy system can be activated, wherein in this operating mode the number and/or the type of the enabled degrees of freedom is predetermined. Such an operating mode can be designated, for example, as a limited movement mode.

Alternatively, it is conceivable that the number and/or the type of the enabled degrees of freedom are adjusted on the basis of the identified identity of at least one marker element. In this case, different numbers and/or different types of enabled degrees of freedom can be assigned to different marker elements.

It is also possible that operating parameters and/or movement parameters, in particular also open-loop or closed-loop parameters for open-loop or closed-loop control of the movement of the microscope, are adjusted on the basis of the detected position or on the basis of an operating mode that is adjusted on a position basis.

This permits enhanced operating safety of the microscopy system since, in predetermined operating scenarios, the number and/or the type of the enabled degrees of freedom and thus also the mobility of the microscope may be limited. In this way, for example, a risk of collision, in particular with a human being, can advantageously be reduced.

In a further exemplary embodiment, a size of a working space of the microscopy system is adjustable, in particular on the basis of the detected position and/or on the basis of the identified identity of at least one marker element. The working space can in this case designate a spatial region in which the microscope of the microscopy system can be moved. The working space can in this case be a space about a reference point, wherein the reference point is formed, for example, by a current spatial position of the microscope (or of a reference point of the microscope) upon activation of an operating mode with a predefined size of the working space. In particular, the reference point can be a geometric center point of the working space.

This permits a further improvement in operating safety by reducing a risk of collision.

Alternatively or in addition, an admissible maximum speed of the movement is adjustable, in particular on the basis of the detected position and/or on the basis of the identified identity of at least one marker element. This and corresponding advantages have already been explained above. This also permits enhanced operational reliability, in particular since undesired movements can be interrupted promptly by the user on account of the set maximum admissible speed.

In this case too, depending on the position, a predetermined operating mode of the microscopy system can be activated, wherein in this operating mode the size of the working space of the microscopy system and/or the admissible maximum speed is predetermined.

In a further exemplary embodiment, a graphic user interface is operated according to the position of the target. This can take place in particular in an operating mode. When such an operating mode is activated, e.g., on the basis of the position of the target, the graphic user interface can be operated according to the position of the target.

The graphic user interface can be a user interface of an application, in particular of a computer-aided application. For example, the user interface can be a user interface for controlling the microscopy system, e.g., for adjustment of operating parameters and/or movement parameters.

The user interface can be displayed by a display device, e.g., a display screen. The display device can in this case serve simultaneously to present the (magnified) image generated by the microscope. In this case, methods for so-called augmented reality can be implemented. However, it is also possible that the user interface is displayed on a display device which does not serve to simultaneously present the (magnified) image generated by the microscope.

For example, the control can involve the position of an image element being adjusted according to the position of the target. The image element can be a cursor, for example. The image element can in this case be part of the user interface. In particular, a position of the image element in the image can be modified according to a change of position of the target. For example, the image element can be moved along a predetermined image direction, e.g., along an image axis, if the target is moved along a predetermined spatial direction. For example, a movement or part of the movement of the target along a transverse axis of the reference coordinate system or of a coordinate system of the image capture device of the position detection device can lead to a movement of the image element along a transverse axis in the image.

Moreover, it is possible that predetermined control commands, e.g., an activation or execution of a selected function or an enlargement/reduction in size of the display, are issued according to the position, in particular the change of position, of the target. For this purpose, control commands can be assigned to positions or changes of position. For example, a (selected) function can be executed when the change of position of the target corresponds to a movement in the form of a double click, i.e., includes two partial movements that do not differ from each other by more than a predetermined extent.

This permits interactive control of computer programs, e.g., a selection of a desired command from a menu.

It is possible that the activated mode or the control performed in the activated mode, e.g., the position tracking explained above, is interrupted if the target is no longer detected or is no longer fully detected. The interrupted mode or the corresponding control can be resumed when the target is detected, in particular completely detected, before the expiry of a predetermined period of time. If no renewed detection takes place before the expiry of the predetermined period of time, renewed activation of the interrupted mode may be necessary, wherein this renewed activation is not effected, or not effected exclusively, by a renewed detection of the target. For example, manual activation may be necessary. However, it is also possible that the interrupted mode or the corresponding control is resumed, independently of the time that has elapsed, when the target is again detected, in particular detected in full. In particular, in the event of a resumption, it may not be necessary in this case to perform a renewed initialization, which takes place for example at the initial activation of the corresponding mode.

A method for operating a microscopy system according to one of the exemplary embodiments described in this disclosure is also provided. The microscopy system is configured in such a way that such a method can be carried out with the microscopy system.

In the method, a position of the at least one target relative to the at least one image capture device of the position detection device is determined. Of course, it is also possible to determine a position of the target in the reference coordinate system explained above, in particular using the transformation rules likewise explained above. Depending on the position that is thus determined, it is also possible to determine a position or change of position of a body part of a user, in particular a hand, of an instrument moved by the user, of a patient or of an item of operating theatre equipment.

Moreover, operation of the microscopy system is controlled according to the determined position or the determined change of position. In particular, a movement, in particular of the microscope, can be controlled according to the determined position. Moreover, an operating parameter and/or a movement parameter of the microscope can be adjusted according to the position. An operating mode of the microscope can also be activated or deactivated according to the position.

Thus, for example, different operating modes of the microscopy system may exist. For example, a movement control mode may exist in which a movement is controlled according to the determined position. For this purpose, the at least one drive device can be actuated in such a way that the microscope executes a desired movement, i.e., a movement with desired movement parameters. A special movement control mode can be the position-tracking mode explained above. In particular, the at least one drive device can be actuated in a position-tracking mode in such a way that a relative movement between the target and the image capture device for position detection is compensated. This may mean that the microscope executes a movement with the same movement parameters of this relative movement, in particular with the same trajectory. In particular, a change of position of the relative position can be determined, wherein the position of the microscope is modified according to this change of position. This may also mean that the microscope is actuated according to a determined position, in particular the determined change of position, in such a way that the relative position between the target, or the object on which the target is arranged, and the microscope remains constant or differs by not more than a predetermined extent from a desired position, for example a starting position. This may also mean that a so-called trajectory servo control is implemented. This serves to compensate for deviations. In trajectory servo control, the microscope follows the movement of the target relative to the image capture device. In this case, the trajectory of this movement is not necessarily duplicated. For example, a speed or an acceleration of the movement of the microscope may be restricted. This may have the effect that, when following the trajectory, the microscope is moved along a trajectory deviating from the trajectory of the movement of the target, e.g., on an orbit with a smaller diameter than an orbit along which the target is moved.

A typical movement mode may be the restricted movement mode explained above.

In a position-tracking mode, and also in movement control modes differing from the latter, a corresponding control can take place. This control can in particular be performed by a corresponding computer unit which performs corresponding algorithms. This means that a user can always look without difficulty, and in the desired manner, into the eyepiece of the microscope.

Moreover, a parameter adjustment mode may also exist, in which an operating parameter and/or a movement parameter of the microscope is adjusted according to the position. As has been explained above, an operating parameter and/or a movement parameter of the microscopy system can also be adjusted according to an identity of an identified marker element. For example, a movement component of the target, which is oriented parallel to the optical axis of the microscope, can be used to adjust an operating parameter of the microscopy system, for example the focus. For example, a movement towards the microscope can reduce a focus value, while a movement away from the microscope increases the focus value.

A further movement component of the target, e.g., a component oriented transversely with respect to the optical axis of the microscope, can be used to adjust a further operating parameter of the microscopy system, for example the zoom value.

In a further operating mode, the position-tracking mode and the parameter adjustment mode can be combined. For example, a movement component of the target, which is oriented parallel to the optical axis of the microscope, can be used to adjust an operating parameter of the microscopy system, for example the focus, wherein movement components perpendicular to this optical axis are utilized for the position tracking. A further operating mode may be the control mode explained above.

A mode, in particular a movement mode, can in this case be activated by corresponding activating means and deactivated by corresponding deactivating means. For example, manual activation and deactivation is possible, e.g., via a hand-operated or foot-operated interface. As has been explained above, activation/deactivation on the basis of a target position is also possible.

A program is also described which, when executed on or by a computer, causes the computer to carry out one, several or all of the steps of the method set out in this disclosure for the operation of a microscopy system. Alternatively or in addition, a program storage medium is described on or in which the program is stored, in particular in a non-temporary form, i.e., in a permanent form. Alternatively or in addition, a computer is described which includes this program storage medium. Moreover, alternatively or in addition, a signal is described, for example a digital signal, which codes information items representing the program and which includes coding means suitable for performing one, several or all of the steps of the method set out in this disclosure for the operation of a microscopy system. The signal can be a physical signal, for example an electrical signal, which in particular is generated technically or by machine.

Moreover, the method for operation of a microscopy system can be a computer-implemented method. For example, one, several or all of the steps of the method can be implemented by a computer. One exemplary embodiment of the computer-implemented method is the use of the computer for performing a data processing technique. For example, the computer can include at least one computing device, in particular a processor, and for example at least one storage device, in order to process the data, in particular technically, for example electronically and/or optically. A computer may in this case be any kind of data processing appliance. A processor may be a semiconductor-based processor. The computing device can in this case be or include the control device explained above.

According to yet another exemplary embodiment, a microscopy system includes a microscope, a stand configured to mount the microscope and including a drive device configured to move the microscope, a position detection device including a target with a marker element and an image capture device configured to optically capture the target, the position detection device being configured to detect a spatial position of the target by evaluating a two-dimensional image captured by the image capture device, a transparent element of the microscope, the transparent element being arranged between the image capture device of the position detection device and the acquisition range to be imaged, the transparent element not serving for a beam guidance and/or beam shaping and/or beam deflection, and a control device configured to control an operation of the microscopy system according to the spatial position of the target detected by the position detection device.

BRIEF DESCRIPTION OF THE DRAWINGS

The disclosure will now be described with reference to the drawings wherein:

FIG. 3 shows a schematic view of a microscopy system according to a further exemplary embodiment of the disclosure, FIG. 4 shows a perspective view of a target, FIGS. 5A to 5D show a schematic plan views of marker elements.

DESCRIPTION OF EXEMPLARY EMBODIMENTS

Identical reference signs hereinafter designate elements having identical or similar technical features.

Figure 1:
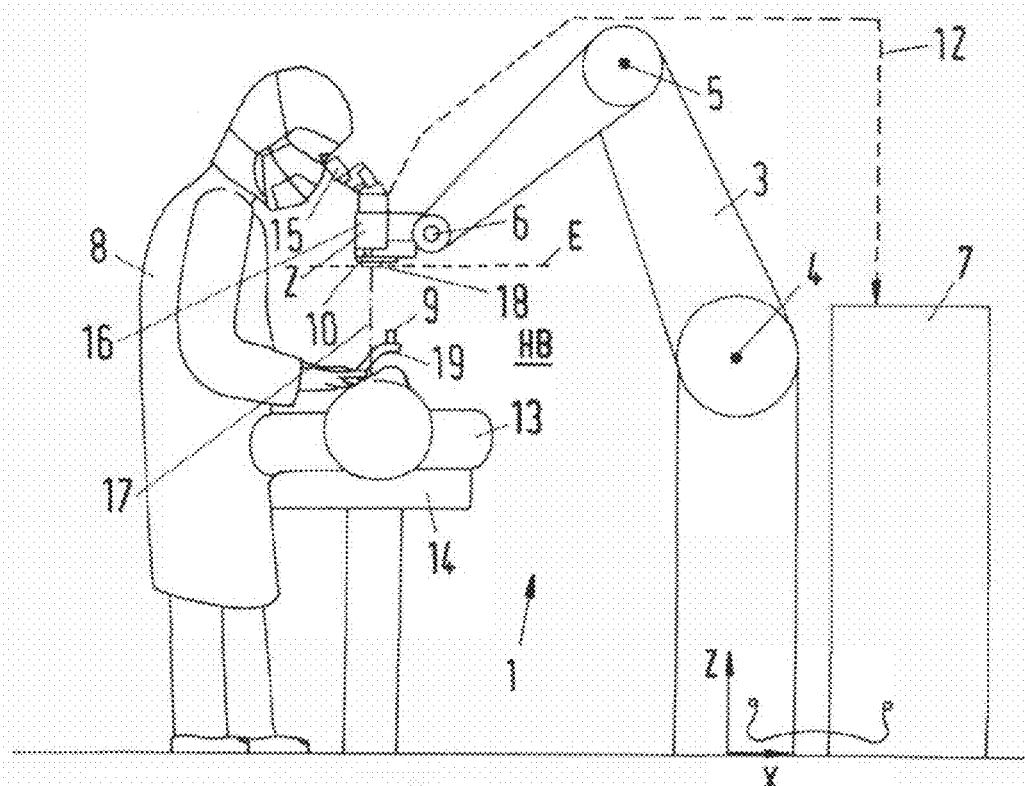
FIG. 1 shows a schematic view of a microscopy system according to a first exemplary embodiment of the disclosure.

FIG. 1 shows a microscopy system 1 according to an exemplary embodiment of the disclosure during use in an operating environment. The microscopy system 1 includes a surgical microscope 2, which is arranged on a stand 3 for mounting the microscope 2, in particular at a free end of the stand 3. The stand 3 permits a movement of the microscope 2 in order to change the position and/or orientation of the microscope 2. A reference coordinate system is depicted with a vertical axis z and a longitudinal axis x. The vertical axis z is here parallel to the direction of a gravitational force and is oriented counter to the latter. The longitudinal axis x is perpendicular to the vertical axis z. A transverse axis (not shown) of the reference coordinate system is here perpendicular to the longitudinal and vertical axes x, z, wherein the axes x, z form a Cartesian coordinate system.

The stand 3 shown is an example of a kinematic structure for mounting and moving the microscope 2. A person skilled in the art will of course know that other kinematic structures may also be used.

The stand 3 includes drive devices (not shown) for moving the microscope 2. Here, the drive devices can, for example, permit a rotational movement of moving parts of the stand 3 about rotation axes 4, 5, 6 and a rotation axis parallel to the vertical axis z. FIG. 1 also shows a control device 7 which serves to control the drive devices (not shown). By the control device 7, the drive devices can be actuated in particular in such a way that the microscope 2 executes a desired movement, in particular in the reference coordinate system. For example, it is possible to place the microscope 2 in a desired spatial position with a desired orientation. Moreover, the control device 7 can also serve to adjust operating parameters and/or movement parameters of the microscope 2, for example to adjust a zoom of the microscope 2. For this purpose, the control device 7 can be connected to the microscope 2 and/or to the drive devices by a signal link and/or data link. Moreover, the control device 7 can also serve to adjust a desired operating mode, for example a movement mode, of the microscope 2.

The microscopy system 1 moreover includes a position detection device for detecting a position of an instrument 19 that can be held and moved by a user 8. The user 8 can be a surgeon, for example. The position detection device includes at least one target 9 with at least one marker element 22 (see FIG. 4 for example) and at least one image capture device 10 for capturing the target. By the position detection device, a position of the target 9 relative to the image capture device can be determined, in particular in a coordinate system of the position detection device. Here, the target 9 includes at least one passive marker element 22, typically three passive marker elements 22.

FIG. 1 shows that the target 9 is fastened to the instrument 19. It is fastened by a suitable holding device, e.g., a clamp holder, with which the target 9 is fastened to the instrument 19 in a manner fixed in position relative to the latter. The instrument 19 can be configured as an aspirator, for example. The instrument 19 is in this case held by the user 8 in such a way that the target 9 is arranged in an acquisition range of the image capture device 10.

The position of the instrument 19 can be detected by the position detection device, by the position of the target 9 being determined, in particular on an image basis, wherein the position of the instrument 19 can then be determined on account of the fixed arrangement of the target 9 on the instrument 19. A relative position between target 9 and instrument 19 may be known beforehand and may be determined, for example, by registration. If only changes of position of the head are to be detected, this registration is not absolutely necessary.

FIG. 1 also shows an image capture device 10 of the microscopy system 1, for example a CCD camera. This image capture device 10 is arranged in a microscope body 16 of the microscope 2. In particular, the image capture device is arranged in a housing of the microscope body 16. Moreover, the image capture device 10 is in particular arranged mechanically rigidly on a part of the microscope 2 and is thus arranged in a fixed position relative to said part.

FIG. 1 also shows a signal link and/or data link 12 between the image capture device 10 and the control device 7. It is possible to determine a relative position between target 9 and image capture device 10 in a three-dimensional coordinate system of the position detection device by the control device 7 or by an evaluation device (not shown), which can be part of the image capture device. For example, it is possible to determine the position of the target 9 in a two-dimensional image coordinate system of the image capture device 10 and then, depending on this position, a position in the coordinate system of the position detection device. Both a position and also an orientation can be determined in the three-dimensional coordinate system of the position detection device. By fastening the target 9 to the instrument 19, it is thus also possible to determine a position of the instrument 19 in the coordinate system of the position detection device and thus also in the reference coordinate system. In particular, a change of position of the target 9 and thus also a change of position of the instrument 19 can be detected by the position detection device.

Before the microscopy system 1 is put into operation, the coordinate system of the position detection device can be registered with the reference coordinate system shown. In other words, a transformation rule can be determined for transforming the position in the coordinate system of the position detection device into the reference coordinate system.

The position of the target 9 can be detected by evaluating exactly one two-dimensional image of the image capture device 10.

Moreover, the depicted control device 7, which can include a microcontroller for example, is configured in such a way that it can actuate the at least one drive device of the stand 3 according to the detected position of the target 9 or according to the detected change of position of the target 9 and thus of the instrument. Alternatively or in addition, at least one operating parameter and/or movement parameter of the microscope 2 or an operating mode of the microscope 2 can be adjusted by the control device 7, as explained above, according to the detected position of the target 9 or according to the detected change of position of the target 9 and thus of the instrument 19.

FIG. 1 also shows a patient 13 lying on an operating table 14. FIG. 1 further shows that the microscope 2 includes an eyepiece 15 into which the user 8 looks in order to view, through the microscope 2, a partial region of the patient 13, in particular with magnification.

In addition, FIG. 1 shows an optical axis 17 of the microscope 2. In a direction of radiation along this optical axis from the patient 13 to the microscope 2, the image capture device 10 is arranged behind a glass plate 18 of the microscope 2, which glass plate 18 closes off the interior of the housing of the microscope body 16 from the external environment. The glass plate 18 is thus arranged between the image capture device 10 and the patient 13 who is to be observed.

FIG. 1 shows a plane E, which delimits a half-space HB. This plane E is oriented perpendicularly with respect to the optical axis 17 of the microscope 2 and runs through a point of intersection between the optical axis 17 and the glass plate 18. Along the optical axis 17, the half-space HB is arranged behind this plane E, wherein the optical axis 17 is oriented from the microscope 2 towards the patient 13. The patient 13 and also the target 9 are arranged in this half-space HB. This can be designated as the target 9 being arranged near the patient.

It is possible, although not shown here, that the image capture device 10 is also arranged inside the housing of the microscope body 16 in such a way that, in the radiation direction, it lies behind a lens of the microscope 2. In this case, the lens and also the glass plate 18 are arranged between the image capture device 10 and the patient 13 who is to be observed.

An acquisition range of the image capture device 10 at least partially overlaps with an acquisition range of the microscope for magnified depiction of the patient or of regions of the body of the patient 13.

By moving the instrument 19, for example with his hands, it is possible that the user 8 moves the target 9 and thus changes the position of the latter. The change of position can be detected here by the position detection device, wherein the control device 7 then controls an operation of the microscopy system 1, in particular of the at least one drive device and/or of the microscope 2, according to the detected position of the target 9. In particular, the movement of the microscope 2 can track the movement of the instrument 19.

Figure 2:
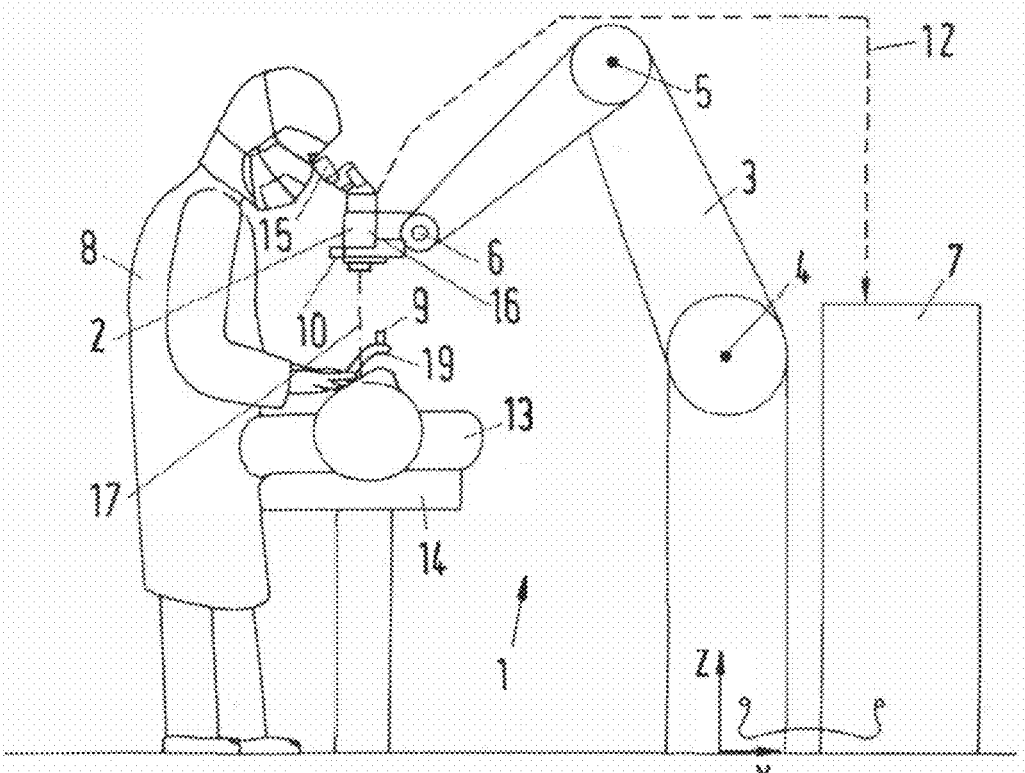
FIG. 2 shows a schematic view of a microscopy system according to a further exemplary embodiment the disclosure.

FIG. 2 shows a schematic view of a microscopy system 1 according to a further exemplary embodiment of the disclosure. The microscopy system 1 shown in FIG. 2 is configured substantially the same way as the microscopy system 1 shown in FIG. 1, and reference may therefore be made to the explanations concerning FIG. 1. In contrast to the embodiment shown in FIG. 1, the image capture device 10 is arranged on, and therefore not in, the housing of microscope body 16. In other words, the image capture device 10 is arranged outside the housing. In particular, no glass plate 18 (see FIG. 1) and/or no optical element of the microscope 2 is arranged between the image capture device 10 and the patient 13 who is to be observed.

The image capture device 10 is here arranged on the microscope 2 in such a way that the image acquisition range at least partially overlaps, or completely overlaps, with the image acquisition range of the microscope 2 for the magnified view.

FIG. 3 shows a schematic view of a microscopy system 1 according to a further exemplary embodiment of the disclosure. This exemplary embodiment is substantially the same as the one shown in FIG. 1, and reference may therefore be made to the corresponding explanation concerning FIG. 1. In contrast to the exemplary embodiment shown in FIG. 1, the microscopy system 1 includes an illumination device 20. The illumination device 20 can in particular be an illumination device 20 that generates light with a wavelength outside the visible range, in particular in the infrared wavelength range. An illumination range of the illumination device 20 can at least partially overlap with an image acquisition range of the image capture device 10. In this way, a target 9 arranged in the image acquisition range can also be illuminated by the illumination device 20.

FIG. 4 shows a perspective view of a target 9 with three marker elements 22. The marker elements 22 are arranged on a support body 23. In particular, the marker elements 22 are not in a collinear arrangement. The marker elements 22 here are of a circular shape or have a circular inner marker surface and a geometric center of this marker surface.

The inner marker surface has varying color values or grey values. In particular, it is filled with color spectrum points, which are distributed radially with respect to the geometric center. A color value or grey value of each color spectrum point of the marker surface is defined, and can thus be determined, according to an angle between a horizontal line through the geometric center and a further line through the geometric center and the corresponding color spectrum point.

FIGS. 5A to 5D show different exemplary embodiments of marker elements 22, namely a first marker element 22a, a second marker element 22b, a third marker element 22c and a fourth marker element 22d. These marker elements 22a, . . . , 22d each have different distributions of color values or grey values. This allows an identity, in particular a unique identity, to be assigned to a marker element 22, 22a, . . . , 22d, which identity is identifiable on an image basis, i.e., by evaluation of the image generated by the image capture device 10.

It is then moreover possible to control the microscopy system 1 shown in FIG. 1 according to the identified identity of the marker element 22, 22a, . . . , 22d. For example, by the control device 7, it is possible to adjust operating parameters and/or movement parameters of the microscope 2 and/or an operating mode of the microscope 2, which parameters and/or mode are assigned to an identified marker element 22a, . . . , 22d. Here, different marker elements 22a, . . . , 22d can be assigned different parameter values.

Figure 6:
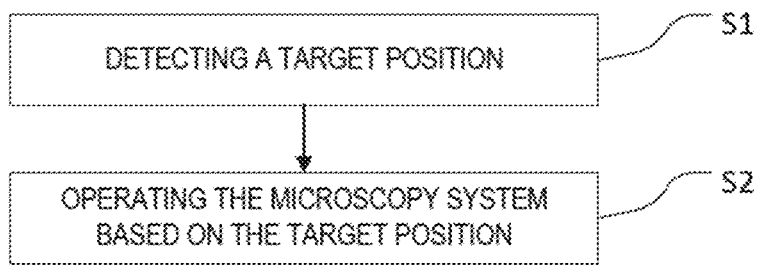
FIG. 6 shows a schematic flow diagram of a method according to an exemplary embodiment of the disclosure.

FIG. 6 shows a schematic flowchart of a method according to a first exemplary embodiment of the disclosure. In a first step S1, a position of at least one target 9 (see FIG. 1 for example) relative to at least one image capture device 10 of the microscopy system 1 shown in FIG. 1 is detected. It is possible that a change of position is also detected here. According to this position, it is then possible to determine a spatial position of a target 9 fastened to a body part or to an instrument 19. It is possible that the target 9 is also fastened to the patient 13 or to the operating table 14. In this case, a spatial position of the patient 13 or of the operating table 14 can be determined according to the position of the target 9.

The spatial position can be determined here in a reference coordinate system (see explanations concerning FIG. 1). In a second step S2, the microscopy system 1 can be operated on the basis of the position thus determined. This has been explained above.

In particular, a movement of the microscope 2 can be controlled on a position basis, in particular in such a way that an optical axis 17 of the microscope 2 is arranged in a desired orientation.

Alternatively or in addition, operating parameters of the microscope, for example a zoom and/or a focus, can be adjusted according to the detected position, in particular the detected change of position, and/or an operating mode of the microscope 2.

In a parameter adjustment mode, a zoom of the microscope 2 can be adjusted, for example, according to the detected relative position. In a movement control mode, a drive device of a stand 3 of the microscopy system 1 can be actuated in such a way that the microscope 2 is controlled with a desired movement. In particular, a change of position of the target 9 can be determined, wherein the drive device can then be actuated in such a way that the microscope 2 executes the same change of position (position tracking mode).

Moreover, it is also possible to control operation of an illumination device 20 (see FIG. 3), for example an intensity of the generated radiation, and/or operation of the image capture device 10. Thus, it is possible that a distance between target 9 and image capture device 10 is determined in the second step S2, wherein an intensity of the illumination by the illumination device 10 and/or a working range of the image capture device 10 is modified according to the distance.

It is moreover possible that an identity of a marker element is identified in the second step S2, in which case the operation of the microscopy system 1, in particular also the movement, is then controlled according to the identified identity.

Figure 7:
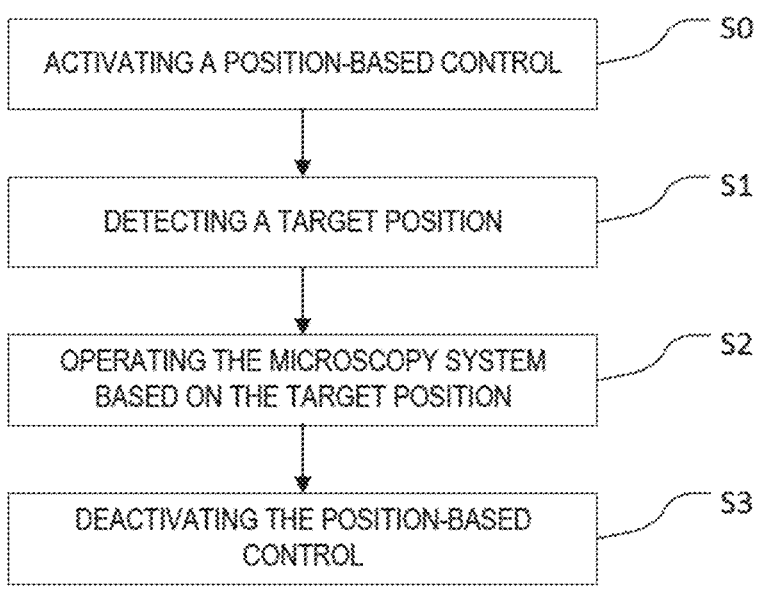
FIG. 7 shows a schematic flowchart of a method according to a further exemplary embodiment of the disclosure.

FIG. 7 shows a schematic flowchart of a method according to a further exemplary embodiment of the disclosure. Here, in an initial step S0 preceding the first step S1, a position-based control of the microscopy system 1 is activated. This can be done, for example, by actuation of an activating means, for example a foot-operated switch.

It is possible that the microscopy system 1 shown in FIG. 1 has for this purpose an activating means (not shown) for activating the position-based control of the microscopy system 1 and/or a means for activating a desired operating mode.

In this case in particular, an evaluation can be made, before or during the second step S2, as to which operating mode is activated. It is also possible to evaluate whether an operating mode is activated and if so which one. Depending on the activated operating mode, further steps of the method can then be carried out. In particular, in the second step S2, movement control is effected only if the microscopy system 1 is in a movement mode that can be controlled on a position basis.

The position-based control or a desired operating mode can be activated, for example, by the user 8 actuating a switch, for example a foot-operated switch, by evaluation of a position or a change of position and/or by identification of a marker element 22.

Moreover, in the initial step S0, it is possible to determine a number and/or type of the degrees of freedom enabled for a movement of the microscope 2.

In regard to the first step S1 and second step S2, reference may be made to the explanations concerning FIG. 6. If position-based control of the microscopy system 1 is no longer intended to take place, then, in a third step S3, the position-based control of the microscopy system 1 can be deactivated, for example by actuation of a corresponding deactivating means. The deactivating means here can be equivalent to the activating means.

It is possible that the position detection is carried out according to a sequence of at least two, typically three, images generated successively by the image capture device 10 (see FIG. 1). For this purpose, in the first step S1, a first image can be generated in a first subsidiary step, a second image can be generated in a subsequent second subsidiary step, and a third image can be generated in a subsequent third subsidiary step. These images can be generated with different imaging parameters or operating parameters of the image capture device 10, for example with different aperture stops.

In summary, microscopy system is provided including a microscope 2, a stand 3 for mounting the microscope 2, wherein the stand 3 comprises at least one drive device for moving the microscope 2, at least one position detection device for detecting a spatial position of a target 9, wherein the position detection device comprises the at least one target 9 with at least one marker element 22, 22a, ..., 22d and an image capture device 10 for optical acquisition of the target 9, at least one control device 7 for controlling the operation of the microscopy system 1 according to the detected position of the target 9, wherein the position detection device is designed to determine the position of the target 9 by evaluating a two-dimensional image generated by the image capture device 10 of the position detection device.

According to an exemplary embodiment, the control device 7 is a control device 7 for controlling the at least one drive device according to the detected position of the target 9 and/or a control device for adjusting at least one operating parameter and/or movement parameter and/or an operating mode of the microscope 2.

According to another exemplary embodiment, the image capture device 10 of the position detection device is arranged in or on the microscope 2 in such a way that beams detected by the image capture device 10 run through at least one optical element of the microscope 2.

According to yet another exemplary embodiment, the image capture device 10 of the position detection device is arranged in or on the microscope 2 in such a way that beams detected by the image capture device 10 do not run through at least one optical element of the microscope 2.

According to an exemplary embodiment, a transparent element of the microscope 2 is arranged between the image capture device 10 of the position detection device and the detection region that is to be imaged.

According to another exemplary embodiment, the position detection can be carried out according to a sequence of at least two images.

According to yet another exemplary embodiment, the sequence can be generated in an HDR method.

According to an exemplary embodiment, the target 9 comprises a marker element 22, 22a, ..., 22d, wherein the marker element 22, 22a, ... 22d has an elliptical marker body or an elliptical marker surface and a geometric center of this marker body or of this marker surface, wherein the marker body or the marker surface is filled with color spectrum points that are distributed radially with respect to the geometric center, wherein a color value of each color spectrum point of the marker/marker surface is determined according to an angle between a horizontal line through the geometric center and a further line through the geometric center and the corresponding color spectrum point.

According to an exemplary embodiment, the position-based control can be performed in real time.

According to another exemplary embodiment, the microscopy system 1 comprises an illumination device 20 for illuminating the target.

According to yet another exemplary embodiment, the illumination device 20 generates light with a wavelength outside the visible range, in particular in the infrared wavelength range.

According to an exemplary embodiment, the intensity of the illumination and/or a working distance and/or an exposure time of the image capture device 10 is adjustable according to the distance of the target 9 from the image capture device 10.

According to an exemplary embodiment, the microscopy system 1 comprises at least one means for filtering the beams detected by the image capture device 10, and/or in that the image capture device 10 only detects beams of a defined wavelength or of a wavelength range, in particular of the infrared wavelength range, and/or in that the image capture device 10 is a monochrome image capture device.

According to another exemplary embodiment, the microscopy system 1 comprises a means for activating a position-based control of the microscopy system.

According to an exemplary embodiment, the image capture device 10 is a wide-angle camera.

According to an exemplary embodiment, an identity is assigned to a marker element 22, 22a, ..., 22d, wherein this identity is identifiable on an image basis.

According to another exemplary embodiment, an operation of the microscopy system 1 is controllable according to the identified identity.

According to yet another exemplary embodiment, an open-loop or closed-loop control of the movement of the microscope 2 is effected according to at least one operating parameter of the microscope 2 and/or at least one operating parameter of the image capture device 10 of the position detection device.

According to an exemplary embodiment, a number and/or a type of the enabled degrees of freedom of the movement of the microscope 2 is adjustable.

According to an exemplary embodiment, a size of a working space of the microscopy system 1 and/or an admissible maximum speed of the movement is adjustable.

According to another exemplary embodiment, a graphic user interface is operated according to the position of the target 9.

According to an exemplary embodiment, a position of the at least one target 9 relative to the at least one image capture device 10 of the position detection device is determined, wherein an operation of the microscopy system 1 is controlled according to the determined position.

In the foregoing description, the terms "exhibit", "have", "comprise" or "include" or any grammatical deviations therefrom are used in a non-exclusive way. Accordingly, these terms can refer either to situations in which, besides the feature introduced by these terms, no further features are present, or to situations in which one or more further features are present. For example, the expression "A exhibits B", "A has B", "A comprises B" or "A includes B" may refer both to the situation in which no further element aside from B is provided in A (that is to say to a situation in which A is composed exclusively of B) and to the situation in which, in addition to B, one or more further elements are provided in A, for example element C, elements C and D, or even further elements.

Furthermore, in the foregoing description the terms "at least one" and "one or more" and grammatical modifications of these terms or similar terms, if they are used in association with one or more elements or features and are intended to express the fact that the element or feature can be provided singly or multiply, in general are used only once, for example when the feature or element is introduced for the first time. When the feature or element is subsequently mentioned again, the corresponding term "at least one" or "one or more" is generally no longer used, without restriction of the possibility that the feature or element can be provided singly or multiply.

Furthermore, in the foregoing description the terms "preferably", "in particular", "by way of example" or similar terms are used in conjunction with optional features, without alternative embodiments thereby being restricted. In this regard, features introduced by these terms are optional features, and there is no intention to restrict the scope of protection of the claims, and in particular of the independent claims, by these features. In this regard, the invention, as will be recognized by the person skilled in the art, can also be carried out using other configurations. Similarly, features introduced by "in one embodiment of the invention" or "in one exemplary embodiment of the invention" are to be understood to be optional features, without this being intended to restrict alternative refinements or the scope of protection of the independent claims. Furthermore, all possibilities of combining the features introduced by these introductory expressions with other features, whether optional or non-optional features, are intended to remain unaffected by said introductory expressions.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS 1 microscopy system
2 microscope
3 stand
4 rotation axis
5 rotation axis
6 rotation axis
7 control device
8 user
9 target
10 image capture device
12 signal link and/or data link
13 patient
14 operating table
15 eyepiece
16 microscope body
17 optical axis
18 glass plate
19 instrument
20 illumination device
22 marker element
22a marker element
22b marker element
22c marker element
22d marker element
23 support device
S0 initial step
S1 first step
S2 second step
S3 third step
E plane
HB half-space

What is claimed is:

1. A microscopy system, comprising:
a microscope having a microscope body with a housing;
a stand configured to mount the microscope and including a drive device configured to move the microscope;
a position detection device including a target with two or more than two marker elements, the marker elements having different identities being identifiable on an image basis, wherein each marker element has an optically detectable pattern, and an image capture device configured to optically capture the target, wherein the position detection device beingis configured to detect a spatial position of the target by evaluating a two-dimensional image captured by the image capture device, wherein the image capture device is arranged in the housing of the microscope body; and
a control device configured to:
control an operation of the microscopy system according to the spatial position of the target detected by the position detection device.

2. The microscopy system according to claim 1, wherein the control device is configured to at least one of (a) control the drive device according to the spatial position of the target, and (b) adjust at least one of an operating parameter, a movement parameter, and an operating mode of the microscope.

3. The microscopy system according to claim 1, wherein the image capture device of the position detection device is arranged in or on the microscope to permit beams detected by the image capture device to run through an optical element of the microscope, or
wherein the image capture device of the position detection device is arranged in or on the microscope to prevent beams detected by the image capture device from running through an optical element of the microscope.

4. The microscopy system according to claim 1, wherein the microscope includes a transparent element arranged between the image capture device of the position detection device and a detection region to be imaged.

5. The microscopy system according to claim 1, wherein position detection is carried out according to a sequence of at least two images.

6. The microscopy system according to claim 5, wherein the sequence of the at least two images is captured by high dynamic range (HDR) imaging.

7. The microscopy system according to claim 1, wherein:
the target includes a marker element,
the marker element has an elliptical marker body or an elliptical marker surface and a geometric center of the elliptical marker body or of the elliptical marker surface,
the marker body or the marker surface is filled with color spectrum points distributed radially with respect to the geometric center, and
a color value of each color spectrum point of the marker/ marker surface is determined according to an angle between a horizontal line through the geometric center, and a further line through the geometric center and the corresponding color spectrum point.

8. The microscopy system according to claim 1, wherein a position-based control is performed in real time.

9. The microscopy system according to claim 1, further comprising an illumination device configured to illuminate the target.

10. The microscopy system according to claim 9, wherein the illumination device generates light with a wavelength outside a visible range in an infrared wavelength range.

11. The microscopy system according to claim 10, wherein at least one of an intensity of an illumination, a working distance, and an exposure time of the image capture device are adjustable according to a distance of the target from the image capture device.

12. The microscopy system according to claim 1, wherein at least one of:
the microscopy system includes a filter configured to filter beams detected by the image capture device,
the image capture device only detects beams of a defined wavelength or of a wavelength range, or
the image capture device is a monochrome image capture device.

13. The microscopy system according to claim 1, further comprising a means for activating a position-based control of the microscopy system.

14. The microscopy system according to claim 1, wherein the image capture device is a wide-angle camera.

15. The microscopy system according to claim 1, wherein an open-loop or closed-loop control of a movement of the microscope is effected according to at least one of an operating parameter of the microscope, and an operating parameter of the image capture device of the position detection device.

16. The microscopy system according to claim 1, wherein at least one of a number and a type of the enabled degrees of freedom of a movement of the microscope and a size of a working space of the microscopy system, and an admissible maximum speed of a movement are adjustable.

17. The microscopy system according to one claim 1, further comprising a graphic user interface operated according to the spatial position of the target.

18. A microscopy system, comprising:
a microscope;
a stand configured to mount the microscope and including a drive device configured to move the microscope;
a position detection device including a target with a marker element and an image capture device configured to optically capture the target, the position detection device being configured to detect a spatial position of the target by evaluating a two-dimensional image captured by the image capture device, wherein the position detection is carried out according to a sequence of at least two images, and wherein a resulting position of the target is determinable as a function of image-specific positions; and
a control device configured to:
control an operation of the microscopy system according to the spatial position of the target detected by the position detection device.

19. A microscopy system, comprising:
a microscope;
a stand configured to mount the microscope and including a drive device configured to move the microscope;
a position detection device including a target with a marker element and an image capture device configured to optically capture the target, the position detection device being configured to detect a spatial position of the target by evaluating a two-dimensional image captured by the image capture device; and
a control device configured to:
control an operation of the microscopy system according to the spatial position of the target detected by the position detection device, wherein at least one of (a) an intensity of an illumination generated by an illumination device of the microscopy system, (b) a working distance of the image capture device, and (c) an exposure time of the image capture device, is adjustable depending on the distance of the target from the image capture device.

20. A microscopy system, comprising:
a microscope;
a stand configured to mount the microscope and including a drive device configured to move the microscope;
a position detection device including a target with a marker element and an image capture device configured to optically capture the target, the position detection device being configured to detect a spatial position of the target by evaluating a two-dimensional image captured by the image capture device;
a filter configured to filter beams detected by the image capture device; and
a control device configured to:
control an operation of the microscopy system according to the spatial position of the target detected by the position detection device, wherein a graphic user interface is operatable according to the position of the target.

* * * * *